(12) United States Patent
Batra et al.

(10) Patent No.: US 7,595,063 B2
(45) Date of Patent: Sep. 29, 2009

(54) COMPRESSED TABLET FORMULATION

(75) Inventors: Udit Batra, Lansdale, PA (US); Raymond J. Higgins, Lansdale, PA (US); Karen C. Thompson, Lansdale, PA (US); Ashok V. Katdare, Norristown, PA (US)

(73) Assignee: Merck & Co., Inc., Rahway, NJ (US)

( * ) Notice: Subject to any disclaimer, the term of this patent is extended or adjusted under 35 U.S.C. 154(b) by 341 days.

(21) Appl. No.: 11/404,357

(22) Filed: Apr. 14, 2006

(65) Prior Publication Data
US 2006/0188570 A1    Aug. 24, 2006

Related U.S. Application Data

(60) Division of application No. 09/894,921, filed on Jun. 28, 2001, now Pat. No. 7,060,294, which is a continuation of application No. 09/312,617, filed on May 17, 1999, now abandoned.

(60) Provisional application No. 60/086,921, filed on May 27, 1998.

(51) Int. Cl.
*A61K 9/20* (2006.01)
*A61K 31/535* (2006.01)

(52) U.S. Cl. .................... 424/464; 424/465; 514/229.8; 514/230.5

(58) Field of Classification Search ................ 424/464, 424/465; 514/229.8, 230.5
See application file for complete search history.

(56) References Cited

U.S. PATENT DOCUMENTS

| | | |
|---|---|---|
| 5,260,073 A | 11/1993 | Phipps et al. |
| 5,519,021 A | 5/1996 | Young et al. |
| 5,663,169 A | 9/1997 | Young et al. |
| 5,665,720 A | 9/1997 | Young et al. |
| 5,856,492 A | 1/1999 | Chen et al. |
| 5,874,430 A | 2/1999 | Christ et al. |
| 5,922,864 A | 7/1999 | Frey et al. |
| 5,965,729 A | 10/1999 | Clarke et al. |
| 5,998,625 A | 12/1999 | Tillyer et al. |
| 6,180,634 B1 | 1/2001 | Vacca et al. |
| 6,238,695 B1 | 5/2001 | Makooi-Morehead et al. |

FOREIGN PATENT DOCUMENTS

| | | |
|---|---|---|
| EP | 0384600 A2 | 8/1990 |
| EP | 0547000 A1 | 6/1993 |
| WO | WO 94/03440 A1 | 2/1994 |
| WO | WO 95/20389 A1 | 8/1995 |
| WO | WO 96/37457 A1 | 11/1995 |
| WO | WO 96/22955 A1 | 8/1996 |
| WO | WO 98/30543 A1 | 7/1998 |
| WO | WO 98/33782 A1 | 8/1998 |
| WO | WO 98/52570 A1 | 11/1998 |
| WO | WO 99/51239 A1 | 10/1999 |

OTHER PUBLICATIONS

Thompson, et al., "Use of an Ephedrine Alkoxide to Mediate Enantioselective Addition of an Acetylide to a Prochiral Ketone: Asymmetric Synthesis of the Reverse Transcriptase Inhibitor L-743,726", Tetrahedron Letters, Vol. 36, pp. 8937-8940 (1995).
Remington: The Science and Practice of Pharmacy. 19th Edition, vol. II, pp. 1616-1620 (1995).
"Los Inhibitorses de La Proteasa Del VIH-1", http://www.previnir.com/salud/sida/inhibid-proteasa.html (1997).
"Tratamientocon Antirretrovirales", http://www.previnir.com/salud/sida/tratamiento.html.
Remington's Pharmaceutical Sciences, pp. 859-869 (1995).
Prescott, L.M., "Antimicrobial Agents and Chemotherapy", vol. X, No. 12, http://thebody.com/bp/dec97/anti.html (1997).
U.S. Appl. No. 09/700,946, filed March 12, 2001, and its prosecution file.
Information Disclosure Statement filed Nov. 10, 2003 for U.S. Appl. No. 09/894,921, filed Jun. 28, 2001, now US 7,060,294.
Information Disclosure Statement filed Oct. 6, 2003 for U.S. Appl. No. 09/894,921, filed Jun. 28, 2001, now US 7,060,294.

*Primary Examiner*—Sreeni Padmanabhan
*Assistant Examiner*—Renee Claytor
(74) *Attorney, Agent, or Firm*—Kenneth R. Walton; Sheldon O. Heber; Valerie J. Camara

(57) ABSTRACT

This invention relates to a 50% drug loaded compressed tablet formulation for efavirenz. Efavirenz is a non-nucleoside reverse trancriptase inhibitor being studied clinically for use in the treatment of HIV infections and AIDS.

9 Claims, No Drawings

COMPRESSED TABLET FORMULATION

This application is a division of U.S. Ser. No. 09/894,921, filed Jun. 28, 2001, now U.S. Pat. No. 7,060,294; which is a continuation of U.S. Ser. No. 09/312,617, filed May 17, 1999 (abandoned); which is a continued prosecution application under 37 C.F.R. § 1.53(d) of U.S. Ser. No. 09/312,617, filed May 17, 1999; which claims the benefit of U.S. Provisional Application No. 60/086,921, filed May 27, 1998.

BACKGROUND OF THE INVENTION

This invention relates to a compressed tablet formulation for efavirenz, which is 50 percent by weight drug loaded and can optionally be film coated. Efavirenz is a non-nucleoside reverse trancriptase inhibitor being studied clinically for use in the treatment of HIV infections and AIDS. A process for the manufacture of the compressed tablet is also disclosed.

The synthesis of efavirenz and structurally similar reverse transcriptase inhibitors are disclosed in U.S. Pat. Nos. 5,519,021, 5,663,169, 5,665,720 and the corresponding PCT International Patent Application WO 95/20389, which published on Aug. 3, 1995. Additionally, the asymmetric synthesis of an enantiomeric benzoxazinone by a highly enantioselective acetylide addition and cyclization sequence has been described by Thompson, et al., Tetrahedron Letters 1995, 36, 8937-8940, as well as the PCT publication, WO 96/37457, which published on Nov. 28, 1996.

Additionally, several applications have been filed which disclose various aspects of the synthesis of (−)-6-chloro-4-cyclopropyl-ethynyl-4-trifluoromethyl-1,4-dihydro-2H-3,1-benzoxazin-2-one including: 1) a process for making the chiral alcohol, U.S. Ser. No. 60/035,462, filed 14 Jan. 1997; 2) the chiral additive, U.S. Ser. No. 60/034,926, filed 10 Jan. 1997; 3) the cyclization reaction, U.S. Ser. No. 60/037,059, filed 12 Feb. 1997; and the anti-solvent crystallization procedure, U.S. Ser. No. 60/037,385 filed 5 Feb. 1997 and U.S. Ser. No. 60/042,807 filed 8 Apr. 1997.

The compressed tablet is an improved formulation which allows one to utilize a tablet over a capsule. The compressed tablet has been demonstrated to have comparable bioavailability data to that seen with the capsule. The key feature of the formulation is the use of a superdisintegrant and disintegrant intragranularly to achieved a bioequivalent formulation. The compressed tablet form was difficult to manage as efavirenz is fragile and the drug loses crystallinity upon compression. This was overcome by adding lactose extragranularly.

SUMMARY OF THE INVENTION

The instant invention relates to a compressed tablet of efavirenz which is a 50 percent drug loaded formulation.

The instant invention also relates to the process for manufacture of the compressed tablet using a wet granulation method.

DETAILED DESCRIPTION OF THE INVENTION

The instant invention relates to a compressed tablet of efavirenz formulation which is 50 percent by weight drug loaded and can optionally be film coated.

The compressed tablet comprises: efavirenz, filler/disintegrant, superdisintegrant, binder, surfactant, filler/compression aid, lubricant, and solvent, wherein of efavirenz is about 50% by weight of the total composition of the compressed tablet.

The efavirenz concentration can be varied from about 1 to about 75% by changing the concentration of remaining excipients. Furthermore, changing the tooling can give a wide ranges of doses, e.g. a 20 mg dose in a 40 mg tablet, a 300 mg dose in a 600 mg tablet, or a 600 mg dose in a 1200 mg compressed tablet, with the same composition. Removing the lactose from the formulation gives about 70% drug in the formulation giving a 600 mg dose in a 860 mg compressed tablet. These variations are very straightforward to effect. This formulation will allow one to formulate efavirenz as a single 600 mg dose as an 860 mg compressed tablet, where as a capsule formulation requires the administration of at least two capsules to dose with 600 mg of efavirenz.

The invention contemplates the use of any pharmaceutically acceptable fillers/compression aids, disintegrants, super-disintegrants, lubricants, binders, surfactants, film coatings, and solvents. Examples of these components are set forth below and are described in more detail in the Handbook of Pharmaceutical Excipients, Second Edition, Ed. A. Wade and P. J. Weller, 1994, The Pharmaceutical Press, London, England.

Fillers and compression aid concentrations can be varied between about 5% to about 80% to complement the drug amount. Examples of fillers/compression aids include: lactose, calcium carbonate, calcium sulfate, compressible sugars, dextrates, dextrin, dextrose, calcium phosphate, kaolin, magnesium carbonate, magnesium oxide, maltodextrin mannitol, powdered cellulose, pregelatinized starch, and sucrose.

Examples of disintegrants include: alginic acid, carboxymethylcellulose calcium, carboxymethylcellulose sodium, colloidal silicon dioxide, croscarmellose sodium, crospovidone, guar gum, magnesium aluminum silicate, methylcellulose, microcrystalline cellulose, polyacrilin potassium, powdered cellulose, pregelatinized starch, sodium alginate and starch.

Examples of fillers (also referred to as a diluent) include: calcium carbonate, calcium sulfate, compressible sugars, confectioner's sugar, dextrates, dextrin, dextrose, dibasic calcium phosphate dihydrate, glyceryl palmitostearate, hydrogenated vegetable oil (type I), kaolin, lactose, magnesium carbonate, magnesium oxide, maltodextrin, mannitol, polymethacrylates, potassium chloride, powdered cellulose, pregelatinized starch, sodium chloride, sorbitol, starch, sucrose, sugar spheres, talc and tribasic calcium phosphate.

Superdisintegrant concentration can be varied between about 1% to about 20% to complement the drug amount and obtain reasonable dissolution. Examples of super-disintegrants include the disintegrants listed above, carboxymethylcellulose sodium, croscarmellose sodium, povidone, guar gum, polacrilin potassium, and pregelatinized starch.

Binder concentration can be varied between 1 and 10% to complement the drug amount. Examples of binders include: acacia, alginic acid, carbomer, carboxymethylcellulose sodium, dextrin, ethylcellulose, gelatin, guar gum, hydrogenated vegetable oil (type I), hydroxyethyl cellulose, hydroxypropyl cellulose, hydroxypropyl methylcellulose, liquid glucose, magnesium aluminaum silicate, maltodextrin, methylcellulose, polymethacrylates, povidone, pregelatinized starch, sodium alginate, starch, and zein.

Examples of surfactants comprises anionic and cationic surfactants, such as sodium lauryl sulfate, docusate sodium (dioctyl sulfosuccinate sodium salt), benzalkonium chloride, benzethonium chloride, and cetrimide (alkyltrimethylammonium bromide, predominantly $C_{14}$ alkyl).

Examples of lubricants include: calcium stearate, glyceryl monostearate, glyceryl palmitostearate, hydrogenated castor oil, hydrogenated vegetable oil, light mineral oil, magnesium stearate, mineral oil, polyethylene glycol, sodium benzoate, sodium lauryl sulfate, sodium stearyl fumarate, stearic acid, talc and zinc stearate.

Examples of solvent comprises: water, ethanol or mixtures thereof.

The compressed tablet can also be film coated. Film coat concentration can be about 1% to about 10% to complement the drug amount, and preferably about 3.1% to about 3.3%. Film coating suspensions include combinations of one, two or three of the following components: carboxymethylcellulose sodium, carnauba wax, cellulose acetate phthalate, cetyl alcohol, confectioner's sugar, ethyl cellulose, gelatin, hydroxyethyl cellulose, hydroxypropyl cellulose, hydroxypropyl methylcellulose, liquid glucose, maltodextrin, methyl cellulose, microcrystalline wax, Opadry and Opadry II, polymethacrylates, polyvinyl alcohol, shellac, sucrose, talc, titanium dioxide, and zein.

The preferred filler/disintegrant is microcrystalline cellulose. The preferred superdisintegrant is croscarmellose sodium. The preferred binder is hydroxypropyl cellulose. A preferred surfactant is sodium lauryl sulfate. The preferred diluent/compression aid is lactose hydrous spray dried. The preferred lubricant is magnesium stearate. The preferred solvent for formulating this compressed tablet is water. The preferred film coating comprises: hydroxypropylcellulose, hydroxypropyl methylcellulose, and titanium dioxide.

The 300 mg film coated efavirenz tablet contains:

| Ingredient | Amt per tablet | Percent w/w |
|---|---|---|
| Core Tablet: | | |
| efavirenz | 300 mg | 50 |
| microcrystalline cellulose NF | 120 mg | 20 |
| hydroxypropyl cellulose LF NF | 19.2 mg | 3.2 |
| croscarmellose sodium | 30 mg | 5 |
| sodium lauryl sulfate | 6 mg | 1 |
| lactose hydrous spray dried (EG) | 118.8 mg | 19.8 |
| magnesium stearate (EG) | 6 mg | 1 |
| Film Coating Material per Tablet: | 3.1% by wt | |
| hydroxypropyl cellulose LF NF | 8.05 mg | 1.4 |
| hydroxypropyl methylcellulose USP 6CPS | 8.05 mg | 1.4 |
| titanium dioxide USP | 3.1 mg | 0.3 |
| Tablet Weight: | 619.2 mg | |

A process for the preparation of a 50% drug loaded compressed tablet comprising the following steps:
(a) blending efavirenz with a filler/disintegrant, super-disintegrant, binder and surfactant;
(b) adding at least 1.1% by weight of water per weight of efavirenz to wet granulate the blended mixture to agglomerate the mixture;
(c) drying the granulated mixture to a moisture content of about 0% to about 10%;
(d) milling the dried mixture to granulate to a uniform size;
(e) blending the milled mixture with a filler/compression aid;
(f) lubricating the blended mixture with a lubricant; and
(g) compressing the lubricated mixture to a compressed tablet of the desired shape.

The process as recited above which comprises the additional step of film coating the compressed tablet with a film coating suspension to produce the desired film coated compressed tablet.

The process as recited above wherein the granulated mixture is dried to a moisture constant of about 2% to about 5%.

A process for the preparation of a 50% drug loaded compressed tablet comprising the following steps:
(a) blending efavirenz with microcrystalline cellulose, sodium lauryl sulfate, hydroxypropyl cellulose and croscarmellose sodium;
(b) adding at least 1.1 weight % water per weight of efavirenz to wet granulate the blended mixture for about 3 minutes to about 8 minutes to agglomerate the mixture;
(c) drying the granulated mixture to a moisture content of about 2% to about 5%;
(d) milling the dried mixture to a granulate of about 250µ to about 75µ;
(e) blending the milled mixture with lactose;
(f) lubricating the blended mixture with magnesium stearate;
(g) compressing the lubricated mixture to a compressed tablet of the desired shape; and
(h) film coating the compressed tablet with a film coating suspension to about 3.1% to about 3.3% of weight of compressed tablet.

The process as recited above wherein the blended mixture is wet granulated for about 6 minutes.

The process as recited above wherein the film coating suspension comprising hydroxypropylcellulose, hydroxypropyl methylcellulose, and titanium dioxide.

Wet granulation can be conducted using granulator mixers, such as a Fielder 10 L high shear granulator mixer, a drum or pan granulator, and a fluid bed granulator. Granulation can also be achieved by conducting dry granulation (without water) using a roller compaction process.

The drying step can be conducted using a Glatt WST-15 fluid bed drier or a tray drier.

The milling step can be conducted using mills such as a Comil or a Fitz mill.

The lubricating and blending steps can be conducted in a V-blender or a ribbon blender.

The compression step to form the tablet can be done a variety of presses including a beta press, single station F-press, the 6-station Korsh, etc.

Film coating can be performed in a Glatt Column coater, a smaller Hi-coater (9"-12" pan), etc.

The formulation also is bioequivalent to a capsule with a smaller dose (200 mg), and more bioavailable than other tablet compositions. The advantages over the capsule include robust processing and sorting steps, smaller size with a larger dose, and market preference. The tablet composition also overcomes the expect loss of crystallinity of efavirenz by adding the lactose extra-granularly while maintaining the dissolution profile.

The increased drug loading often compromises the dissolution profile of the drug. This hurdle was overcome by including the super-disintegrant intragranularly, as well as the disintegrant intragranularly. The lactose was added extra-ganularly to maintain the crystallinity of efavirenz.

This formulation was determined to be bioequivalent to the capsule formulation being used in clinical trials. The wet granulation process has been used to optimize the formulation such that about 80% dissolution of the drug occurs within 10 minutes in a 1% Sodium Dodecyl sulfate (SDS) solution, while stirring at a 50 rpm paddle speed.

Preparation of (−)-6-chloro-4-cyclopropylethynyl-4-trifluoromethyl-1,4-dihydro-2H-3,1-benzoxazin-2-one (currently referred to by its generic name efavirenz or code name DMP-266)

Scheme 1 outlines the key steps in the synthesis of (−)-6-chloro-4-cyclopropylethynyl-4-trifluoromethyl-1,4-dihydro-2H-3,1-benzoxazin-2-one (efavirenz). The chiral addition step allows for the enantioselective addition of the cyclopropylacetylide across the trifluoromethylketone of 1. The p-methoxybenzyl (PMB)-protected amino alcohol, 2, produced is then deprotected to give the amino alcohol, 3. The amino alcohol is then cyclized using a chloroformate and base to give efavirenz.

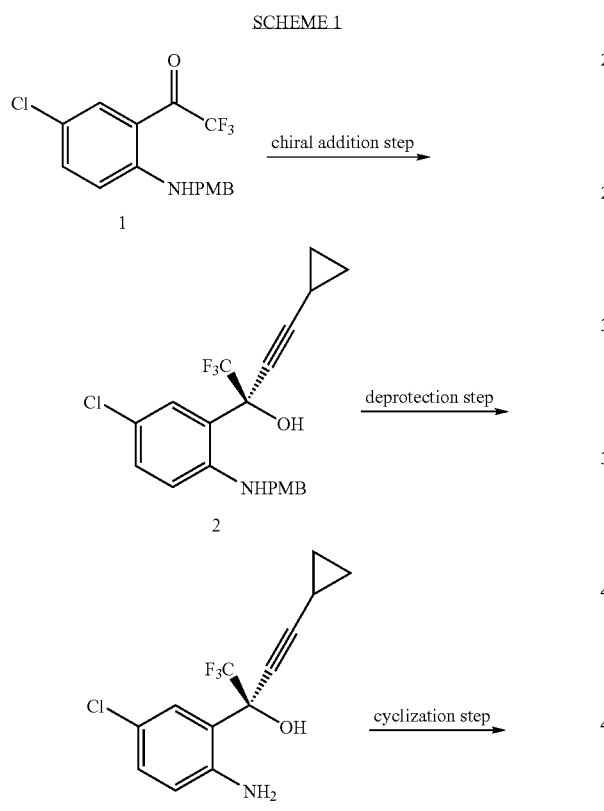

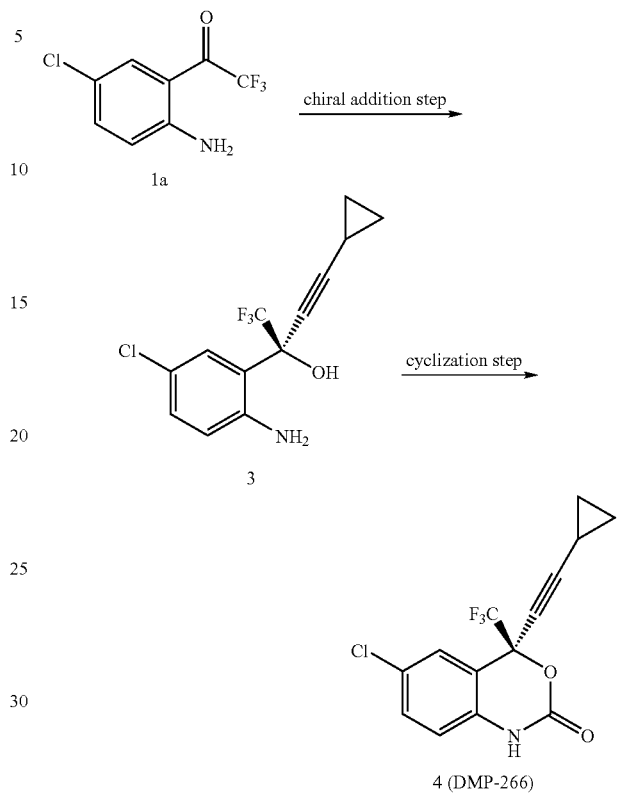

Scheme 2 outlines the preparation of efavirenz using an alternative process which is a chiral addition reaction. The new chiral addition reaction allows for the elimination of the protection-deprotection sequence as outlined in Scheme 1.

Scheme 3 describes the process for the synthesis of the chiral intermediate used in the preparation of efavirenz. This reaction has been demonstrated to work using about 1.2 equivalents of cyclopropylacetylene and chiral additive, much less than the prior methods. The numerous chiral additives have been run and give high yields with a commerically available chiral ligand, such as N-methyl ephedrine and N-pyrrolidinyl norephedrine.

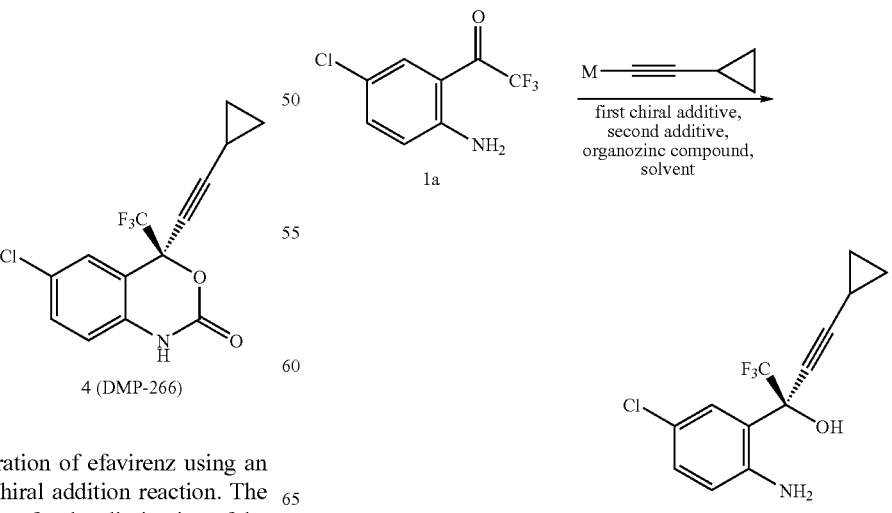

The cyclization of the amino alcohol, 3 to produce the 1,4-dihydro-2H-3,1-benzoxazin-2-one, 4 is outlined in Scheme 4 below. The reaction can be carried out as a one-step process, or alternatively a two step process with the potential isolation of the intermediate carbamate, 5 depending upon the chloroformate utilized. It has been demonstrated that the aryl chloroformates form less stable carbamates such that when they are treated with aqueous base they cyclize to the product, in a one-step process. The alkyl chloroformate, alternatively, provides an alkyl carbamate, a key intermediate capable of being isolated and purified prior to carrying out the cyclization step. Based upon the stability of the alkyl carbamates, a viable two step process for the preparation of efavirenz has been developed which comprises the formation of the alkyl carbamate intermediate, 5 followed by the cyclization of the carbamate to give the desired product, 4. Additionally, it has been demonstrate that phosgene can also be used.

-continued

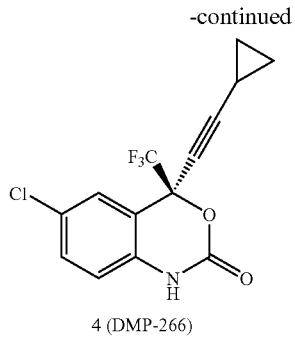

4 (DMP-266)

The compressed tablet is formulated following the sequence of steps outlined in Scheme 5.

SCHEME 4

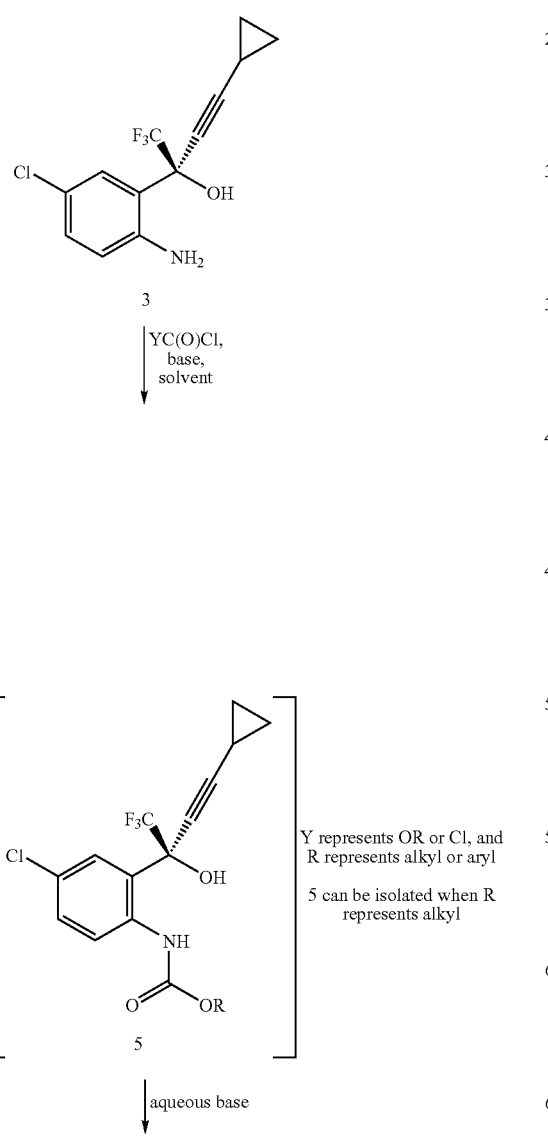

Y represents OR or Cl, and R represents alkyl or aryl 5 can be isolated when R represents alkyl

SCHEME 5 efavirenz, filler/disintegrant, superdisintegrant, binder, surfactant

↓

| High Shear Blend |
solvent

↓

| Wet Granulate |

↓

| Fluid Bed Dry |

↓

| Mill |
filler/compression aid

↓

| Blend |
lubricant

↓

| Lubricate |

↓

| Compress |
Film Coating Suspension

⋮

| Film Coat |

The following examples are meant to be illustrative of the present invention. These examples are presented to exemplify the invention and are not to be construed as limiting the scope of the invention.

EXAMPLE 1

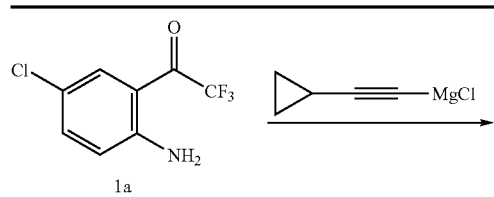

1a

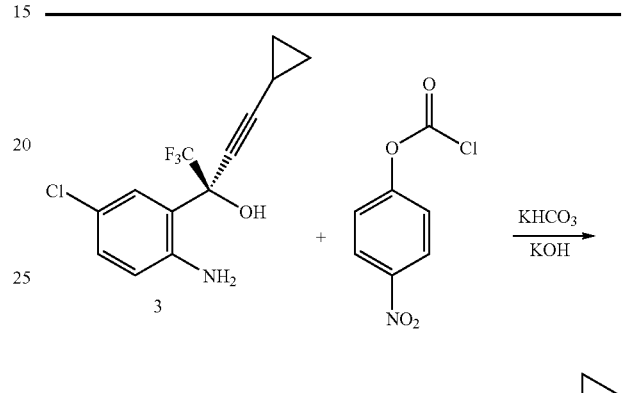

3

| Materials | Amount | Mol | MW |
|---|---|---|---|
| Ketone 1a | 1.00 kg | 4.47 | 223.58 |
| (1R, 2S)-N-pyrrolidinyl norephedrine | 1.35 kg | 6.58 | 205.30 |
| cyclopropyl acetylene | 361.9 g | 5.47 | 66.10 |
| n-BuMgCl (2.0 M in THF) | 2.68 L | 5.37 | |
| 2,2,2-trifluoroethanol (99%) | 429.5 g | 4.29 | 100.04 |
| ZnEt$_2$ (0.892 M in hexane) | 6.02 L | 5.37 | |
| THF | 9.36 L | | |
| 30% K$_2$CO$_3$ | 550 mL | | |
| 30% citric acid | 2.0 L | | |
| Toluene (for crystallization, 2 mL/g of 4) | 2.6 L | | |
| Heptane (for crystallization, 4 mL/g of 4) | 5.2 L | | |

To a solution of trifluoroethanol and (1R, 2S)-N-pyrrolidinyl norephedrine in THF (9 L) under nitrogen is added a solution of diethylzinc in hexane at 0° C. slowly enough to keep the temperature below 30° C. The mixture is stirred at room temperature for 0.5~1 h. In another dry flask a solution of chloromagnesium cyclopropyl acetylide is prepared as follows: To neat cyclopropyl acetylene at 0° C. is added a solution of n-butylmagnesium chloride slowly enough to keep the internal temperature ≦30° C. The solution is stirred at 0° C. for ~40 min and transferred to the zinc reagent via cannula with 0.36 L of THF as a wash. The mixture is cooled to −10° C. and ketoaniline 1a is added. The mixture is stirred at −2 to −8° C. for 35 h, warmed to room temperature, stirred for 3 h, and quenched with 30% potassium carbonate over 1.5 h. The mixture is stirred for 4 h and the solid is removed by filtration and washed with THF (2 cake volume). The wet solid still contains ~18 wt % of pyrrolidinyl norephedrine and is saved for further study. The filtrate and wash are combined and treated with 30% citric acid. The two layers are separated. The organic layer is washed with water (1.5 L). The combined aqueous layers are extracted with 2.5 L of toluene and saved for norephedrine recovery. The toluene extract is combined with the organic solution and is concentrated to ~2.5 L. Toluene is continuously feeded and distilled till THF is not detectable by GC. The final volume is controlled at 3.9 L. Heptane (5.2 L) is added over 1 h. The slurry is cooled to 0° C., aged for 1 h, and filtered. The solid is washed with heptane (2 cake volume) and dried to give 1.234 Kg (95.2% yield) of amino alcohol 3 as a white crystalline. The material is 99.8 A % pure and 99.3% ee.

EXAMPLE 2

| | FW | g | mL | mmol | equiv |
|---|---|---|---|---|---|
| amino alcohol 3 | 289 | 100 | | 346 | 1 |
| 4-nitrophenylchloroformate | 201.6 | 73.2 | | 363 | 1.05 |
| KHCO$_3$ | 100 | 45 | | 450 | 1.3 |
| 2N KOH | 56 | | 346 | 692 | 2.0 |
| H$_2$O | | | 654 | | |
| MTBE | | | 500 | | |

To a three necked round bottom flask, equipped with a mechanical stirrer, nitrogen line, and thermocouple, was charged the solid amino alcohol 3, MTBE (500 mL), and aqueous KHCO$_3$ (45 g in 654 mL H$_2$O). Solid 4-nitrophenyl chloroformate was added, in 4 batches, at 25° C. During the addition the solution pH was monitored. The pH was maintained between 8.5 and 4 during the reaction and ended up at 8.0. The mixture was stirred at 20-25° C. for two hours. Aqueous KOH (2N) was added over 20 minutes, until the pH of the aqueous layer reached 11.0.

The layers were separated and 500 mL brine was added to the MTBE layer. 0.1 N Acetic acid was added until the pH was 6-7. The layers were separated and the organic phase was washed with brine (500 mL). At this point the mixture was solvent switched to EtOH/IPA and crystallized as recited in Examples 5 and 6.

EXAMPLE 3

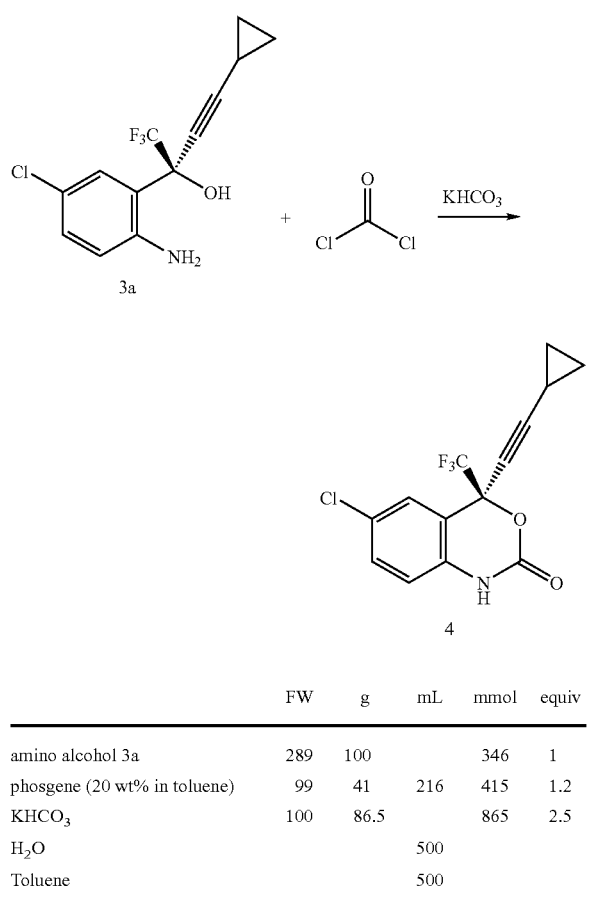

| | FW | g | mL | mmol | equiv |
|---|---|---|---|---|---|
| amino alcohol 3a | 289 | 100 | | 346 | 1 |
| phosgene (20 wt% in toluene) | 99 | 41 | 216 | 415 | 1.2 |
| KHCO$_3$ | 100 | 86.5 | | 865 | 2.5 |
| H$_2$O | | | 500 | | |
| Toluene | | | 500 | | |

To a three necked round bottom flask, equipped with a mechanical stirrer, nitrogen line, and thermocouple, was charged the solid amino alcohol 3a, toulene (500 mL), and aqueous KHCO$_3$ (86.5 g in 500 mL H$_2$O). Phosgene solution in toulene was added at 25° C., and the mixture was stirred at 20-25° C. for two hours.

The layers were separated and the organic phase was washed with brine (500 mL). At this point the mixture was solvent switched to EtOH/IPA and crystallized as recited in Examples 5 and 6.

EXAMPLE 4

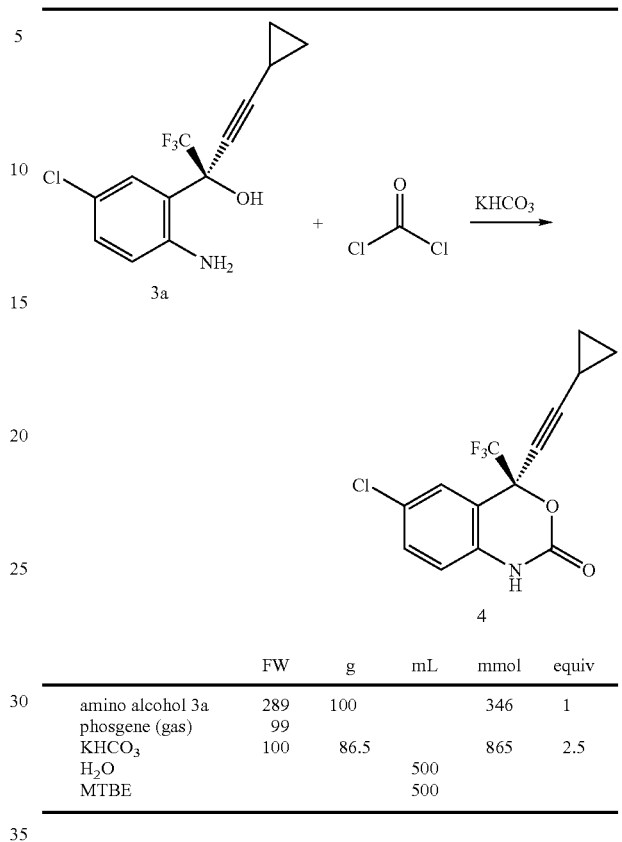

| | FW | g | mL | mmol | equiv |
|---|---|---|---|---|---|
| amino alcohol 3a | 289 | 100 | | 346 | 1 |
| phosgene (gas) | 99 | | | | |
| KHCO$_3$ | 100 | 86.5 | | 865 | 2.5 |
| H$_2$O | | | 500 | | |
| MTBE | | | 500 | | |

To a three necked round bottom flask, equipped with a mechanical stirrer, nitrogen line, and thermocouple, was charged the solid amino alcohol 3a, MTBE (500 mL), and aqueous KHCO$_3$ (86.5 g in 500 mL H$_2$O). Phosgene gas was slowly passed into the solution at 25° C., until the reaction was complete.

The layers were separated and the organic phase was washed with brine (500 mL). At this point the mixture was solvent switched to EtOH/IPA and crystallized as recited in Examples 5 and 6.

EXAMPLE 5

Crystallization of Efavirenz from 30% 2-Propanol in Water using a Ratio of 15 ml Solvent Per Gram Efavirenz Using Controlled Anti-Solvent Addition on a 400 g Scale.

400 g. of efavirenz starting material is dissolved in 1.8 L of 2-propanol. The solution is filtered to remove extraneous matter. 1.95 L of deionized (DI) water is added to the solution over 30 to 60 minutes. 10 g. to 20 g. of efavirenz seed (Form II wetcake) is added to the solution. The seed bed is aged for 1 hour. The use of Intermig agitators is preferred to mix the slurry. If required (by the presence of extremely long crystals or a thick slurry), the slurry is wet-milled for 15-60 seconds. 2.25 L of DI water is added to the slurry over 4 to 6 hours. If required (by the presence of extremely long crystals or a thick slurry), the slurry is wet-milled for 15-60 seconds during the addition. The slurry is aged for 2 to 16 hours until the product concentration in the supernatant remains constant. The slurry is filtered to isolate a crystalline wet cake. The wet cake is Washed with 1 to 2 bed volumes of 30% 2-propanol in water and then twice with 1 bed volume of DI water each. The washed wet cake is dried under vacuum at 50° C.

EXAMPLE 6

Crystallization of Efavirenz from 30% 2-Propanol in Water using a Ratio of 15 ml Solvent Per Gram Efavirenz Using a Semi-Continuous Process on a 400 g Scale.

400 g. of efavirenz starting material is dissolved in 1.8 L of 2-propanol. A heel slurry is produced by mixing 20 g. of Form II efavirenz in 0.3 L of 30% (v/v) 2-propanol in water or retaining part of a slurry from a previous crystallization in the crystallizer. The dissolved batch and 4.2 L of DI water are simultaneously charged to the heel slurry at constant rates over 6 hours to maintain a constant solvent composition in the crystallizer. Use of Intermig agitators during the crystallization is preferred. During this addition the slurry is wet-milled when the crystal lengths become excessively long or the slurry becomes too thick. The slurry is aged for 2 to 16 hours until the product concentration in the supernatant remains constant. The slurry is filtered to isolate a crystalline wet cake. The wet cake is washed with 1 to 2 bed volumes of 30% 2-propanol in water and then twice with 1 bed volume of DI water each. The washed wet cake is dried under vacuum at 50° C.

EXAMPLE 7

Preparation of Amino Alcohol 3 and ee Upgrading—Through Process

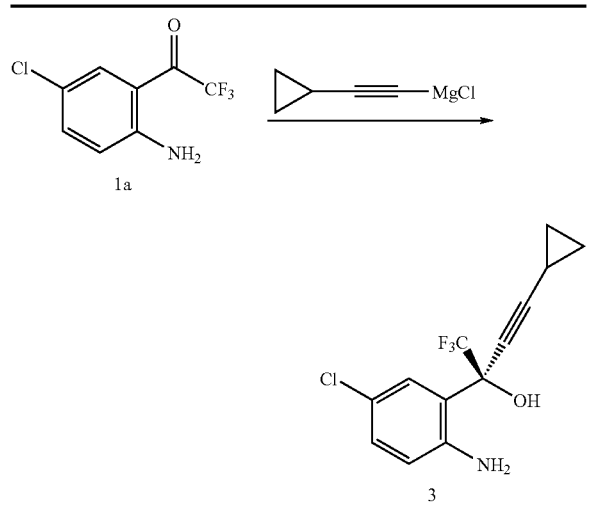

| Materials | Amount | Mol | MW |
| --- | --- | --- | --- |
| Ketone 1 | 1.00 kg | 4.47 | 223.58 |
| (1R, 2S)-N-Pyrrolidinyl norephedrine | 1.35 kg | 6.58 | 205.30 |
| Cyclopropyl acetylene | 361.9 g | 5.47 | 66.10 |
| n-BuMgCl (2.0 M in THF) | 2.68 L | 5.37 | |
| Trifluoroethanol (99%) | 429.5 g | 4.29 | 100.04 |
| ZnEt$_2$ (0.892 M in hexane) | 6.02 L | 5.37 | |
| THF | 9.36 L | | |
| 30% K$_2$CO$_3$ | 1.2 L | | |
| 1 M Citric acid | 3.5 L | | |
| Heptane | 12 L | | |
| Isopropyl acetate (IPAc) | 40 L | | |
| 12N HCl | 405 mL | 4.88 | |
| tert-Butyl methyl ether (MTBE) | 6 L | | |

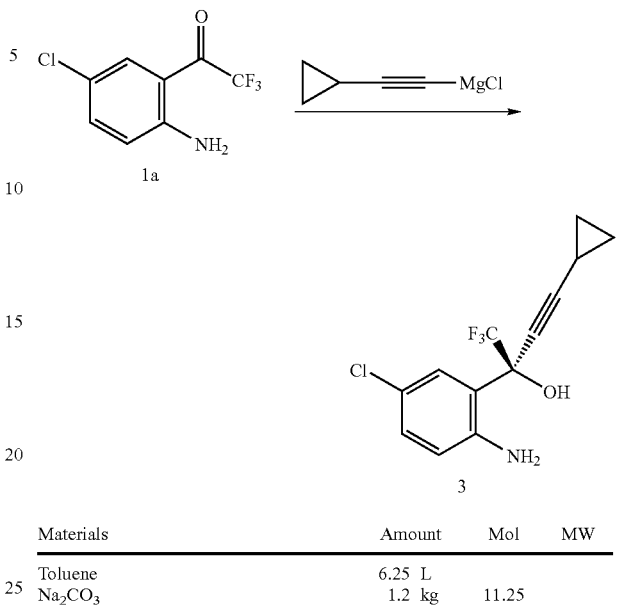

| Materials | Amount | Mol | MW |
| --- | --- | --- | --- |
| Toluene | 6.25 L | | |
| Na$_2$CO$_3$ | 1.2 kg | | 11.25 |

A solution of diethyl zinc in hexane was added to a solution of trifluoroethanol (429.5 g, 4.29 mol) and (1R, 2S)-N-pyrrolidinyl norephedrine (1.35 kg, 6.58 mol) in THF (9 L), under nitrogen, at 0° C. The resulting mixture was stirred at room temperature for approx. 30 min. In another dry flask a solution of chloromagnesium-cyclopropylacetylide was prepared as follows. To a solution of n-butylmagnesium chloride in THF (2 M, 2.68 L, 5.37 mol) was added neat cyclopropylacetylene at 0° C. keeping the temperature ≦25° C. The solution was stirred at 0° C. for 1~2 h. The solution of chloromagnesiumcyclopropylacetylide was then warmed to room temperature and was transferred into the zinc reagent via cannula over 5 min followed by vessel rinse with 0.36 L of THF. The resulting mixture was aged at ~30° C. for 0.5 h and was then cooled to 20° C. The ketoaniline 1 (1.00 kg, 4.47 mol) was added in one portion as a solid, and the resulting mixture was stirred at 20-28° C. for 3 h.

The reaction was quenched with 30% aq. potassium carbonate (1.2 L) and aged for 1 h. The solid waste was filtered and the cake was washed with THF (3 cake volumes). The filtrate and wash were combined and solvent switched to IPAc.

The IPAc solution of product 3 and pyrrolidinyl norephedrine was washed with citric acid (3.5 L) and with water (1.5 L). The combined aqueous layers were extracted with IPAc (2 L) and saved for norephedrine recovery. To the combined organic layers was added 12N HCl (405 mL, 4.88 mol), to form a thin slurry of the amino alcohol-HCl salt. The mixture was aged for 30 min at 25° C. and was then dried azeotropically.

The slurry was aged at 25° C. for 30 min and filtered. The cake was washed with 2.5 L of IPAc and dried at 25° C. under vacuum/nitrogen for 24 h to give 1.76 kg of the wet HCl salt.

The salt was dissolved in a mixture of MTBE (6 L) and aq Na$_2$CO$_3$ (1.18 kg in 6.25 L water). The layers were separated and the organic layer was washed with 1.25 L of water. The organic layer was then solvent switched into toluene.

Heptane (5 L) was added over 1 h at 25° C. The slurry was cooled to 0° C., aged for 1 h, and filtered. The solid was washed with heptane (2 cake volumes) and was dried to give 1.166 kg (90% overall yield) of amino alcohol 3 as a white crystalline solid.

Norephedrine Recovery

The aqueous solution was basified to pH13 using 50% aq NaOH, and extracted with heptane (2 L). The heptane solution was washed with water (1 L) and concentrated to remove residual IPAc and water. The final volume was adjusted to about 3 L. The heptane solution was cooled to −20° C., aged for 2 h, and filtered. The solid was washed with cold heptane (1 cake volume) and dried to give 1.269 kg solid (94% recovery).

EXAMPLE 8

| 50% Drug-Loaded Compressed tablet Of Efavirenz | |
|---|---|
| Ingredient | Amt per batch |
| Core Tablet: | |
| efavirenz | 950 g |
| microcrystalline cellulose NF | 380 g |
| hydroxypropyl cellulose LF NF | 60.8 g |
| croscarmellose sodium | 95 g |
| sodium lauryl sulfate | 19 g |
| lactose hydrous spray dried (EG)* | 19.8% w/w |
| magnesium stearate (EG)* | 1% w/w |
| water | 1.045 L |
| Film Coating Material per Tablet: | 3.3% by wt of tablet |
| hydroxypropyl cellulose LF NF | 8.54 mg (2.5%) |
| hydroxypropyl methylcellulose USP 6CPS | 8.54 mg (2.5%) |
| titanium dioxide USP | 3.42 mg (1%) |
| water | (94%) |

*EG = extragranular

Efavirenz (950 g) was blended with microcrystalline cellulose (380 g), sodium lauryl sulfate (19 g), hydroxypropyl cellulose (60.8 g) and croscarmellose sodium (95 g) in a Fielder 10 L high shear granulator mixer for four minutes. At least about 1.1 weight % water per weight of efavirenz (1.045 L) was added to wet granulate the blended mixture over about 6 minutes to about 8 minutes to agglomerate the mixture using an appropriate spray nozzle. The granulated mixture is dried to a moisture content of about 2% to about 5% in a Glatt WST-15 fluid bed drier. The dried mixture was milled using a 40 G round screen in a Comil. The milled mixture was blended in a V-Blender with lactose for 4 minutes (calculated amount is the amount needed to make the final composition contain 19.8% lactose by weight). The blended mixture was lubricated with magnesium stearate (calculated amount is the amount needed to make the final composition contain 1% magnesium stearate by weight) in the V-Blender for 3 minutes. The lubricated mixture was compressed using a beta press to give a compressed tablet of the desired shape. The compressed tablets were film coated with an aqueous coating suspension that contains 2.5% hydroxypropyl cellulose (HPC); 2.5% hydroxymethylcellulose (HPMC); and 1% titanium dioxide (TiO$_2$) and 94% water by weight percent in a 19" O'Hara pan coater to a coat weight of about 3.3% per tablet. Note that the coat is the dried form of the suspension.

What is claimed is:

1. A process for the preparation of a drug loaded compressed tablet containing about 50% efavirenz comprising the following steps:
   (a) blending efavirenz with a filler/disintegrant, superdisintegrant, binder and surfactant;
   (b) adding at least 1.1% by weight of water per weight of efavirenz to wet granulate the blended mixture to agglomerate the mixture;
   (c) drying the granulated mixture to a moisture content of about 0% to about 10%;
   (d) milling the dried mixture to granulate to a uniform size;
   (e) blending the milled mixture with a filler/compression aid;
   (f) lubricating the blended mixture with a lubricant; and
   (g) compressing the lubricated mixture to a compressed tablet of the desired shape;
   wherein the superdisintegrant is croscarmellose sodium and has a concentration in the tablet between about 1% to about 5% by weight.

2. The process as recited in claim 1 which comprises the additional step of film coating the compressed tablet with a film coating suspension to produce the desired film coated compressed tablet.

3. The process as recited in claim 2 wherein the granulated mixture is dried to a moisture content of about 2% to about 5%.

4. A process for the preparation of a drug loaded film coated compressed tablet containing about 50% efavirenz comprising the following steps:
   (a) blending efavirenz with microcrystalline cellulose, sodium lauryl sulfate, hydroxypropyl cellulose and croscarmellose sodium as a superdisintegrant;
   (b) adding at least 1.1 weight % water per weight of efavirenz to wet granulate the blended mixture for about 3 minutes to about 8 minutes to agglomerate the mixture;
   (c) drying the granulated mixture to a moisture content of about 2% to about 5%;
   (d) milling the dried mixture to a granulate of about 250μ to about 75μ;
   (e) blending the milled mixture with lactose;
   (f) lubricating the blended mixture with magnesium stearate;
   (g) compressing the lubricated mixture to a compressed tablet of the desired shape, wherein the superdisintegrant has a concentration in the tablet between about 1% to about 5% by weight; and
   (h) film coating the compressed tablet with a film coating suspension to about 1% to about 10% by weight of the weight of compressed tablet.

5. The process as recited claim 4, wherein the blended mixture is wet granulated for about 6 minutes.

6. The process as recited claim 5, wherein the film coating suspension comprises hydroxypropylcellulose, hydroxypropyl methylcellulose, and titanium dioxide.

7. The process as recited claim 6, wherein the compressed tablet is film coated with the film coating suspension to about 3.1% to about 3.3% by weight of the weight of compressed tablet.

8. A process for preparing a compressed tablet comprising crystalline efavirenz, filler/disintegrant, superdisintegrant, binder, surfactant, diluent/compression aid, and lubricant, which comprises:
   (a) blending a mixture of the crystalline efavirenz, filler/disintegrant, superdisintegrant, binder and surfactant;

(b) adding water to the blended mixture to obtain a wet granulate;
(c) drying the wet granulate;
(d) milling the dried granulate;
(e) blending the milled granulate with a filler/compression aid;
(f) lubricating the blend; and
(g) compressing the lubricated blend to obtain the compressed tablet, wherein the efavirenz is about 50% by weight of the total composition of the compressed tablet and the superdisintegrant is croscarmellose sodium and has a concentration in the tablet between about 1% to about 5% by weight and the filler/compression aid is lactose.

9. A process according to claim 8, wherein:
the filler/disintegrant is microcrystalline cellulose;
the binder is hydroxypropyl cellulose;
the surfactant is sodium lauryl sulfate; and
the lubricant is magnesium stearate.

* * * * *